United States Patent [19]
Ramakrishnan

[11] Patent Number: 6,043,076
[45] Date of Patent: Mar. 28, 2000

[54] GENE ENCODING 2,3-DIHYDROXYBENZOIC ACID DECARBOXYLASE

[75] Inventor: Santha Ramakrishnan, Sunnyvale, Calif.

[73] Assignee: Board of Regents of University of Nebraska, Lincon, Nebr.

[21] Appl. No.: 09/136,073

[22] Filed: Aug. 18, 1998

Related U.S. Application Data

[60] Provisional application No. 60/056,621, Aug. 20, 1997.
[51] Int. Cl.$^7$ .............................. C12N 9/88; C12N 15/00; C12N 1/20; C12N 5/00; C12P 19/34
[52] U.S. Cl. .................. 435/232; 435/320.1; 435/252.3; 435/91.1; 435/325; 536/23.1; 536/23.2; 536/23.5
[58] Field of Search ................................ 435/232, 320.1, 435/325, 252.3, 91.1; 536/23.1, 23.2, 23.5

[56] References Cited

U.S. PATENT DOCUMENTS

| | | | |
|---|---|---|---|
| 5,272,073 | 12/1993 | Frost et al. | 435/155 |
| 5,616,496 | 4/1997 | Frost et al. | 435/252.3 |
| 5,629,181 | 5/1997 | Frost et al. | 435/156 |

OTHER PUBLICATIONS

R. Santha et al., "2,3–Dihydroxybenzoic Acid Decarboxylase from *Aspergillus Niger*: Mechanism, Cloning and Overexpression," *FASEB Journal*, vol. 11, No. 9, Jul. 31, 1997, p. A1017.

Dunn, G.E., *Organic Chemistry*, vol. 3, Elsevier Sci. Pub. Co., 1977, Chap. 1, "Carbon–13 Kinetic Isotope Effects in Decarboxylation," pp. 1–40.

March., J., *Advanced Organic Chemistry*, 3d ed., John Wiley, New York, 1985, pp. 507–509.

Kamath, A.V., Dasgupta, D., and Vaidyanathan, C.S., "Enzyme–Catalysed Non–Oxidative Decarboxylation of Aromatic Acids: I. Purification and Spectroscopic Properties of 2,3–Dihydroxybenzoic Acid Decarboxylase from *Aspergillus Niger*," *Biochem. Biophys. Res. Comm.*, vol. 145, No. 1, May 1987, pp. 586–595.

Santha, R., Rao, N.A., Vaidyanathan, C.S., "Identification of the Active–Site Peptide of 2,3–dihydroxybenzoic Acid Decarboxylase from *Aspergillus Oryzae*," *Biochim. Biophys. Acta*, 1293 (1996) 191–200.

O'Leary, M.H., "Determination of Heavy–Atom Isotope Effects on Enzyme–Catalyzed Reactions," *Methods in Enzymology*, vol. 64, 1980, pp. 84–104.

Kamath, A. and Vaidyanathan, C.S., "New Pathway for the Biodegradation of Indole in *Aspergillus Niger*," *Appl. Env. Microbiol.*, vol. 56, No. 1, Jan. 1990, pp. 275–280.

Kamath, A.V., Rao, N.A., and Vaidyanathan, C.S., "Enzyme Catalysed Non–Oxidative Decarboxylation of Aromatic Acids: II. Identification of Active Site Residues of 2,3–Dihydroxybenzoic Acid Decarboxylase from Aspergillus Niger," *Biochem. Biophys. Res. Comm.*, vol. 165, No. 1, Nov. 1989, pp. 20–26.

Santha, R., Savithri, H.S., Rao, N.A., and Vaidyanathan, C.S., "2,3–Dihydroxybenzoic Acid Decarboxylase from *Aspergillus Niger*," *Eur. J. Biochem.*, 230, 1995, pp. 104–110.

Santha, R., Dickman, M.B., and O'Leary, M.H., "2,3–Dihydroxybenzoic Acid Decarboxylase from Aspergillus Niger: Mechanism, Cloning and Overexpression," Poster presented at the 17th International Union of Biochemistry and Molecular Biology Congress, San Francisco, CA, Aug. 24–29, 1997.

Kamath, A. et al., Biochem. Biophys. Res. Comm., vol. 145, No. 1, pp. 586–595, May 1987.

Mierendorf, R. et al., inNovations, Newsletter of Novagen, Inc., vol. 1 No. 1, pp. 1–3, May. 1994.

Lee, C. et al., Science, vol. 239, pp. 1288–1291, Mar. 1988.

*Primary Examiner*—Ponnathapu Achutamurthy
*Assistant Examiner*—Peter P. Tung
*Attorney, Agent, or Firm*—Shook, Hardy & Bacon L.L.P.

[57] ABSTRACT

The enzyme 2,3-dihydroxybenzoic acid decarboxylase has industrial applications for the decarboxylation of ring mounted carboxyls, specifically the decarboxylation of 2,3-dihydroxybenzoic acid to catechol. This invention relates to the isolation of a nucleic acid sequence from *Aspergillus niger* that encodes an enzyme that decarboxylates 2,3-dihydroxybenzoic acid. This invention further discloses the nucleic acid sequence, the protein sequence, vectors comprising the nucleic acid sequence, cells transformed with the nucleic acid sequence, and methods for the production of 2,3-dihydroxybenzoic acid decarboxylase.

6 Claims, 1 Drawing Sheet

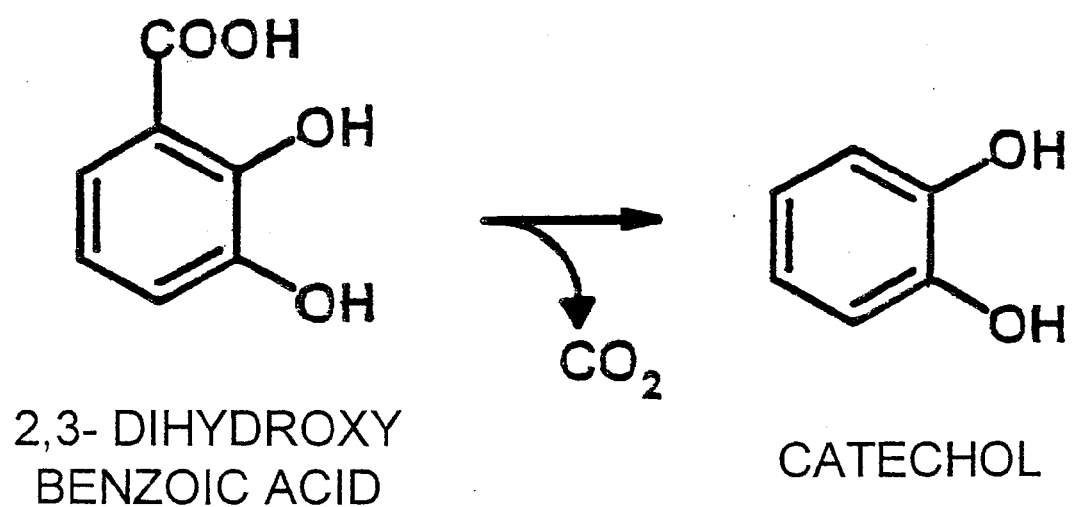

SEQUENCE LISTING

```
<160> NUMBER OF SEQ ID NOS: 5

<210> SEQ ID NO 1
<211> LENGTH: 1096
<212> TYPE: DNA
<213> ORGANISM: Aspergillus niger
<220> FEATURE:
<221> NAME/KEY: gene
<222> LOCATION: 1-1096
<220> FEATURE:
<221> NAME/KEY: CDS
<222> LOCATION: 1-1029
<220> FEATURE:
<221> NAME/KEY: polyA_site
<222> LOCATION: 1073
<220> FEATURE:
<221> NAME/KEY: polyA_signal
<222> LOCATION: 1056-1061
<220> FEATURE:
<221> NAME/KEY: 3' UTR
<222> LOCATION: 1027-1073
<220> FEATURE:
<221> NAME/KEY: source/Aspergillus niger
<222> LOCATION: 1-1096
<300> PUBLICATION INFORMATION:
<301> AUTHORS: Santha, Ramakrishnan
```

-continued

```
       Dickman, Martin B.
       O'Leary, Marion H.
<302>  TITLE: 2,3-Dihydroxybenzoic Acid Decarboxylase From Aspergillus
       niger: Mechanism, Cloning And Overexpression.
<303>  JOURNAL: Faseb Journal
<304>  VOLUME: 11
<305>  ISSUE: 9
<306>  PAGES: A1017
<307>  DATE: 1997-07-31

<400>  SEQUENCE: 1 atg ttg ggt aag atc gcc ctc gaa gaa gcc ttc gcg ctt ccc cgc ttc         48
Met Leu Gly Lys Ile Ala Leu Glu Glu Ala Phe Ala Leu Pro Arg Phe
1               5                   10                  15 gaa gag aag aca cgc tgg tgg gcc agt cta ttc tcc gtc gac ccc gaa         96
Glu Glu Lys Thr Arg Trp Trp Ala Ser Leu Phe Ser Val Asp Pro Glu
            20                  25                  30 acc cac gtc aag gag atc acc gac atc aac aag ctg cgc atc gaa cat        144
Thr His Val Lys Glu Ile Thr Asp Ile Asn Lys Leu Arg Ile Glu His
        35                  40                  45 gcc gac aag tac ggc gtg gga tac cag atc ctc tcc tac aca gct ccc        192
Ala Asp Lys Tyr Gly Val Gly Tyr Gln Ile Leu Ser Tyr Thr Ala Pro
 50                  55                  60 ggt gtc caa gac att tgg gat ccc gtt gaa gcc caa gcc cta gcc gtt        240
Gly Val Gln Asp Ile Trp Asp Pro Val Glu Ala Gln Ala Leu Ala Val
65                  70                  75                  80 gaa atc aac gac tac atc gca gag cag atc cgc gac aag ccc gat cgc        288
Glu Ile Asn Asp Tyr Ile Ala Glu Gln Ile Arg Asp Lys Pro Asp Arg
                85                  90                  95 ttt ggc gca ttt gca acc ctc tcc atg cac aac ccc caa gaa gcc gcc        336
Phe Gly Ala Phe Ala Thr Leu Ser Met His Asn Pro Gln Glu Ala Ala
            100                 105                 110 tct gag ctc cgc cgc tgc gtc caa acc tac ggc ttc aaa ggc gcc cta        384
Ser Glu Leu Arg Arg Cys Val Gln Thr Tyr Gly Phe Lys Gly Ala Leu
        115                 120                 125 gta aac gac acc caa cgc gcc ggc ccc gac ggc gac gac atg atc ttc        432
Val Asn Asp Thr Gln Arg Ala Gly Pro Asp Gly Asp Asp Met Ile Phe
    130                 135                 140 tac gac aac gcc tcc tgg gat atc ttc tgg caa aca tgc acg gaa ctc        480
Tyr Asp Asn Ala Ser Trp Asp Ile Phe Trp Gln Thr Cys Thr Glu Leu
145                 150                 155                 160 gac gtc cct ctg tac ttg cac cct cgc aac ccc acc ggc acc atc tac        528
Asp Val Pro Leu Tyr Leu His Pro Arg Asn Pro Thr Gly Thr Ile Tyr
                165                 170                 175 gag aag ctc tgg gca gac cgg aaa tgg ctc gtg ggt ccg ccg ctc agc        576
Glu Lys Leu Trp Ala Asp Arg Lys Trp Leu Val Gly Pro Pro Leu Ser
            180                 185                 190 ttc gcg cag ggc gtc agt ctg cac gtt ctg ggg atg gtc acg aac ggc        624
Phe Ala Gln Gly Val Ser Leu His Val Leu Gly Met Val Thr Asn Gly
        195                 200                 205 gtg ttt gat cgt cac ccc aac cta cag ctc att atg ggt cat cta ggt        672
Val Phe Asp Arg His Pro Asn Leu Gln Leu Ile Met Gly His Leu Gly
    210                 215                 220 gaa cat gtg ccg ttt gat atg tgg cgc att aat cat tgg ttc gag gac        720
Glu His Val Pro Phe Asp Met Trp Arg Ile Asn His Trp Phe Glu Asp
225                 230                 235                 240 cgc aag aag ttg ttg ggg ttg gcg gag acg tgt aag aag acg att cgg        768
Arg Lys Lys Leu Leu Gly Leu Ala Glu Thr Cys Lys Lys Thr Ile Arg
                245                 250                 255 gag tac ttt gct cag aat atc tgg att acg act tct ggg cac ttt tcg        816
Glu Tyr Phe Ala Gln Asn Ile Trp Ile Thr Thr Ser Gly His Phe Ser
            260                 265                 270
```

```
acg acc acg ttg aac ttc tgc atg gcg gag gtc ggg gtc gat cgc att    864
Thr Thr Thr Leu Asn Phe Cys Met Ala Glu Val Gly Val Asp Arg Ile
            275                 280                 285 ttg ttc tcg att gat tat ccg ttc gag acg ttt gag gat gcg tgt gtt    912
Leu Phe Ser Ile Asp Tyr Pro Phe Glu Thr Phe Glu Asp Ala Cys Val
            290                 295                 300 tgg ttt gat ggc gcg gag ttg aat ctt tcc gat aag gct aag gtc ggg    960
Trp Phe Asp Gly Ala Glu Leu Asn Leu Ser Asp Lys Ala Lys Val Gly
305                 310                 315                 320 agg gat aat gcg gcg agg ttg ttt aag ttg ggg gcg ttt agg gat tat   1008
Arg Asp Asn Ala Ala Arg Leu Phe Lys Leu Gly Ala Phe Arg Asp Tyr
                325                 330                 335 gat gcg aag gtt aag gct tag gttgggaact aggattaatg gaatgaaata      1059
Asp Ala Lys Val Lys Ala
                340 aatatgactg tttttgaaa aaaaaaaaaa aaaaaaa                           1096

<210> SEQ ID NO 2
<211> LENGTH: 342
<212> TYPE: PRT
<213> ORGANISM: Aspergillus niger
<220> FEATURE:
<221> NAME/KEY: INIT_MET
<222> LOCATION: 1
<220> FEATURE:
<221> NAME/KEY: ACT_SITE
<222> LOCATION: 251
<300> PUBLICATION INFORMATION:
<301> AUTHORS: Santha, Ramakrishnan
       Dickman, Martin B.
       O'Leary, Marion H.
<302> TITLE: 2,3-Dihydroxybenzoic Acid Decarboxylase From Aspergillus
       niger: Mechanism, Cloning And Overexpression.
<303> JOURNAL: Faseb Journal
<304> VOLUME: 11
<305> ISSUE: 9
<306> PAGES: A1017
<307> DATE: 1997-07-31
<308> DATABASE ACCESSION NUMBER: SWISSPROT Accession no. P80346
       (fragments of 2,3-dihydroxybenzoic
<309> DATABASE ENTRY DATE: 1995-11-01

<400> SEQUENCE: 2

Met Leu Gly Lys Ile Ala Leu Glu Glu Ala Phe Ala Leu Pro Arg Phe
1               5                   10                  15

Glu Glu Lys Thr Arg Trp Trp Ala Ser Leu Phe Ser Val Asp Pro Glu
                20                  25                  30

Thr His Val Lys Glu Ile Thr Asp Ile Asn Lys Leu Arg Ile Glu His
            35                  40                  45

Ala Asp Lys Tyr Gly Val Gly Tyr Gln Ile Leu Ser Tyr Thr Ala Pro
        50                  55                  60

Gly Val Gln Asp Ile Trp Asp Pro Val Glu Ala Gln Ala Leu Ala Val
65                  70                  75                  80

Glu Ile Asn Asp Tyr Ile Ala Glu Gln Ile Arg Asp Lys Pro Asp Arg
                85                  90                  95

Phe Gly Ala Phe Ala Thr Leu Ser Met His Asn Pro Gln Glu Ala Ala
            100                 105                 110

Ser Glu Leu Arg Arg Cys Val Gln Thr Tyr Gly Phe Lys Gly Ala Leu
        115                 120                 125

Val Asn Asp Thr Gln Arg Ala Gly Pro Asp Gly Asp Met Ile Phe
    130                 135                 140

Tyr Asp Asn Ala Ser Trp Asp Ile Phe Trp Gln Thr Cys Thr Glu Leu
```

```
                    145                 150                 155                 160
Asp Val Pro Leu Tyr Leu His Pro Arg Asn Pro Thr Gly Thr Ile Tyr
                165                 170                 175

Glu Lys Leu Trp Ala Asp Arg Lys Trp Leu Val Gly Pro Pro Leu Ser
            180                 185                 190

Phe Ala Gln Gly Val Ser Leu His Val Leu Gly Met Val Thr Asn Gly
        195                 200                 205

Val Phe Asp Arg His Pro Asn Leu Gln Leu Ile Met Gly His Leu Gly
    210                 215                 220

Glu His Val Pro Phe Asp Met Trp Arg Ile Asn His Trp Phe Glu Asp
225                 230                 235                 240

Arg Lys Lys Leu Leu Gly Leu Ala Glu Thr Cys Lys Lys Thr Ile Arg
                245                 250                 255

Glu Tyr Phe Ala Gln Asn Ile Trp Ile Thr Thr Ser Gly His Phe Ser
            260                 265                 270

Thr Thr Thr Leu Asn Phe Cys Met Ala Glu Val Gly Val Asp Arg Ile
        275                 280                 285

Leu Phe Ser Ile Asp Tyr Pro Phe Glu Thr Phe Glu Asp Ala Cys Val
    290                 295                 300

Trp Phe Asp Gly Ala Glu Leu Asn Leu Ser Asp Lys Ala Lys Val Gly
305                 310                 315                 320

Arg Asp Asn Ala Ala Arg Leu Phe Lys Leu Gly Ala Phe Arg Asp Tyr
                325                 330                 335

Asp Ala Lys Val Lys Ala
            340

<210> SEQ ID NO 3
<211> LENGTH: 30
<212> TYPE: DNA
<213> ORGANISM: Artificial Sequence
<220> FEATURE:
<223> OTHER INFORMATION: Synthetic

<400> SEQUENCE: 3
ataagaatgc ggccgctttt tttttttttt                                           30

<210> SEQ ID NO 4
<211> LENGTH: 24
<212> TYPE: DNA
<213> ORGANISM: Artificial Sequence
<220> FEATURE:
<223> OTHER INFORMATION: Synthetic

<400> SEQUENCE: 4
ggaattcatg ytbggyaaga tcgc                                                 24

<210> SEQ ID NO 5
<211> LENGTH: 23
<212> TYPE: DNA
<213> ORGANISM: Artificial Sequence
<220> FEATURE:
<223> OTHER INFORMATION: Synthetic

<400> SEQUENCE: 5
aattcatatg ttgggtaaga tcg                                                  23
```

GENE ENCODING 2,3-DIHYDROXYBENZOIC ACID DECARBOXYLASE

CROSS REFERENCE TO RELATED APPLICATIONS

This application claims the benefit of U.S. Provisional Application Ser. No. 60/056,621, which was filed with the U.S. Patent and Trademark Office on Aug. 20, 1997.

STATEMENT REGARDING FEDERALLY-SPONSORED RESEARCH OR DEVELOPMENT

Not applicable.

BACKGROUND OF THE INVENTION

This invention relates to the isolation of a nucleic acid sequence that encodes an enzyme capable of removing carboxyl groups from aromatic rings. In particular the enzyme decarboxylates 2,3-dihydroxybenzoic acid to form catechol.

The decarboxylation reaction involves the non-oxidative removal of a carboxyl group from an aromatic ring. Aromatic rings containing a carboxyl group are chemically challenging to work with because the carboxyl group is a deactivating group. Deactivating groups make electrophilic substitutions on aromatic rings difficult. Therefore, the removal of a deactivating carboxyl group from an aromatic ring has a great deal of potential in the chemical industry.

Catechol is an aromatic compound utilized in the development of pharmaceuticals such as L-DOPA(L-3,4-dihydroxyphenylalanine) and adrenaline, agrobiochemicals such as carbofuran, and antioxidants such as 4-tert-butyl catechol and veratrol. Additionally, catechol is utilized in the production of flavorants such as vanilla and polymerization inhibitors. The current global noncaptive market for catechol is $20.5 \times 10^6$ Kg/yr.

Current commercial production of aromatics has several drawbacks. One disadvantage relates to the starting material utilized in aromatic production. Most aromatics are synthesized from benzene, toluene and xylene which are derived from petroleum or natural gas fossil fuel feedstocks. For example, catechol is currently produced by distillation of coal tar or the hydroxylation of phenol. Both of these methods require fossil fuels as starting material. Fossil fuels are nonrenewable and therefore more expensive than renewable resources. In addition, many countries do not have a large national supply of fossil fuels for the derivation of aromatic compounds.

In addition to cost, the use of fossil fuels has a negative impact on the environment. Petroleum based processes for the production of aromatics often require hazardous starting materials. One example of a hazardous starting material is benzene, which is a carcinogen. These processes also produce hazardous waste by-products that can inadvertently leak into the environment Hazardous waste by-products also need to be disposed of or stored, adding to the costs of operation.

Another problem with current aromatic compound production is that the synthetic procedures involve harsh reaction conditions. Current methods for the removal of carboxyl groups from aromatic rings involve high temperatures and acid conditions in the presence of metal catalysts. These extreme reaction conditions are expensive energy consuming procedures that pose industrial and environmental safety concerns and dramatically increase the cost of the aromatics.

Therefore, a method for the production of aromatics, and specifically catechol, is needed to overcome the problems associated with current methods utilized in the production of aromatics.

SUMMARY OF THE INVENTION

Accordingly, it is an object of the present invention to provide an alternative method for the removal of carboxyl groups form aromatic rings. In particular, it is an object of the present invention to provide a method for the decarboxylation of 2,3dihydroxybenzoic acid to form catechol. Specifically, the invention provides an isolated nucleic acid sequence encoding a stable enzyme that will catalyze the non-oxidative decarboxylation of 2,3-dihydroxybenzoic acid to catechol.

Another object of the present invention is to provide an isolated nucleic acid sequence encoding a protein that catalyzes the non-oxidative decarboxylation of 2,3-dihydroxybenzoic acid to catechol and that hybridizes, under stringent conditions, to SEQ. ID. NO. 1. SEQ. ID. NO. 1 comprises a nucleic acid sequence that encodes *Aspergillus niger* 2,3-dihydroxybenzoic acid decarboxylase.

Yet another object of the present invention is to provide an isolated nucleic acid sequence encoding a protein that catalyzes the non-oxidative decarboxylation of 2,3-dihydroxybenzoic acid to catechol and that hybridizes under stringent conditions to a nucleic acid sequence corresponding to an amino acid sequence of SEQ. ID. NO. 2.

A further object of the present invention is to provide fragments of the nucleic acid sequence encoding 2,3-dihydroxybenzoic acid decarboxylase that hybridize to SEQ. ID. NO. 1 and that code for products that maintain biological activity necessary to decarboxylate 2,3-dihydroxybenzoic acid. These fragments can be either recombinant or synthetic or a combination thereof.

A further object of the present invention is to provide a recombinant vector comprising a nucleic acid sequence encoding a protein that catalyzes the non-oxidative decarboxylation of 2,3-dihydroxybenzoic acid to catechol. The definition of a vector for the purposes of this invention is any nucleic acid sequence into which a foreign nucleic acid sequence may be inserted wherein the nucleic acid sequence containing the foreign nucleic acid sequence may be used to introduce the foreign nucleic acid sequence into a host cell. This vector may also comprise regulatory elements operably linked to the nucleic acid sequence.

A further object of the present invention is to provide various cells transformed with the vector comprising a nucleic acid sequence encoding a protein that catalyzes the non-oxidative decarboxylation of 2,3-dihydroxybenzoic acid to catechol.

A further object of the present invention is to provide methodology for the production of the various products of the present invention. Examples include isolated nucleic acid sequences encoding 2,3-dihydroxybenzoic acid decarboxylase, isolated 2,3-dihydroxybenzoic acid decarboxylase, isolated SEQ. ID. NO. 1, isolated SEQ. ID. NO. 2, and the protein product of SEQ. ID. NO.:1.

A further object of the present invention is to illustrate the use of an enzyme for the synthesis of catechol and the decarboxylation of aromatic acids. This approach reduces environmental concerns associated with traditional methods for the production of aromatics.

2,3-dihydroxybenzoic acid decarboxylase of the present invention is suited to accomplish these and other related objects of the present invention by catalyzing a reaction whereby a carboxyl group is removed from an aromatic ring. Specifically, a carboxyl group is removed from 2,3-dihydroxybenzoic acid to produce catechol and carbon dioxide. This decarboxylation is unusual in that it involves a non-oxidative decarboxylation from an aromatic nucleus and does not require a cofactor. This enzyme is found in the fungus *Aspergillus niger* and functions in the pathway for the metabolism of indole. This enzyme is listed in the Enzyme Commission by the no. EC.4.1.1.46

*Aspergillus niger* is a known fungus and is readily available to those with ordinary skill in the art. Additionally, *Aspergillus niger* has been deposited with the American Type Culture Collection (ATCC), 10801 University Boulevard, Manassas, Va. 20110-2209. The deposit was filed with ATCC on Aug. 10, 1998. The culture is identified as *Aspergillus niger* CSVInd and by the ATCC Accession No. 74460. Additionally, the pET22b(+)DHBD vector, as described in this specification, has been deposited with the ATCC, 10801 University Boulevard, Manassas, Va. 20110-2209. The deposit was filed with ATCC on Aug. 10, 1998. The vector is identified as pET22b(+)DHBD and by the ATCC Accession No. 203104. These deposited materials are available pursuant to all requirements of the United States Patent and Trademark Office.

Additional objects, advantages and novel features of the invention will be set forth in part in the description which follows and in part will be apparent to those skilled in the art upon examination of the following or may be learned by practice of the invention.

BRIEF DESCRIPTION OF THE DRAWINGS

The accompanying drawing forms a part of this specification and is to be read in conjunction therewith.

FIG. 1 illustrates the decarboxylation reaction whereby 2,3-dihydroxybenzoic acid decarboxylase catalyzes the decarboxylation of 2,3-dihydroxybenzoic acid to catechol.

DETAILED DESCRIPTION OF THE PREFERRED EMBODIMENTS OF THE INVENTION

An isolated nucleic acid sequence encoding 2,3-dihydroxybenzoic acid decarboxylase is disclosed. Additionally, synthetic oligonucleotides used in isolating the sequence encoding 2,3-dihydroxybenzoic acid decarboxylase are disclosed.

Nucleic acid sequences presented by this disclosure will enable the creation of full-length nucleic acid molecules encoding 2,3-dihydroxybenzoic acid decarboxylase and fragments thereof. Specifically, the disclosed oligonucleotides of SEQ. ID. NOs. 3–5, or any other sequences that hybridize to the ends of SEQ.ID.NO.1, may be utilized to produce copies of the disclosed nucleic acid sequence which may be used for the expression of the disclosed protein Additionally, it is well-known by those of ordinary skill in the art that oligonucleotide design allows an unlimited choice for incorporating restriction endonuclease sites into a vector and a product The flexibility in oligonucleotide selection and restriction endonuclease site selection allows several choices for the method of preparation of the nucleic acid sequences of the present invention.

It is also well-known to practitioners of the art that the nucleic acid sequences may be recombinant or synthetic or partly synthetic and partly recombinant. Recombinant implies the use of molecular biology tools. Synthetic refers to the use of chemical synthetic procedures.

Isolated products of the present invention are disclosed. These products include but are not limited to nucleic acids, peptides and proteins. The term "nucleic acid" includes both DNA and RNA sequences. Some examples of DNA and RNA sequences include cDNA and mRNA, respectively. An example of a protein product is the translated protein product of SEQ.ID.NO.1.

The present invention discloses vectors containing the nucleic acid sequences encoding 2,3-dihydroxybenzoic acid decarboxylase. In one embodiment, the vector includes regulatory sequences operably positioned within the vector, whereby the nucleic acid sequences encoding 2,3-dihydroxybenzoic acid decarboxylase are expressed. These vectors used for expressing a given protein, or a portion thereof, are commonly referred to as expression vectors. Often, these expression vectors comprise at least one origin of replication, at least one promoter, at least one ribosome binding site and at least one terminator. Vectors may often contain many other sequence elements known to those of ordinary skill in the art. These vectors may be of viral, procaryotic or eukaryotic origin and may serve a variety of functions not limited to expression.

The present invention discloses cells transformed with various vectors. In one embodiment, this cell is an *E. coli* cell of the appropriate genetic makeup, transformed with an expression vector of the present invention is capable of expressing 2,3-dihydroxybenzoic acid decarboxylase. Such cells, commonly known as host cells, can be either procaryotic or eukaryotic. It is understood by those of ordinary skill in the art that a recombinant molecule containing the nucleic acid sequences of the present invention can be used to transform a variety of hosts using any known technique for transformation. Additionally, there are other methods besides transformation for the introduction of nucleic acids into host cells. These methods include, but are not limited to, transfection and direct introduction of nucleic acid sequences.

In addition to the nucleic acid sequences, vectors, and transformed cells, the present invention further discloses a method for the production of 2,3-dihydroxybenzoic acid decarboxylase. This method involves the insertion of a nucleic acid sequence that encodes 2,3-dihydroxybenzoic acid decarboxylase into an expression vector. This vector may then be transformed into an appropriate host bacterial cell so that the nucleic acid sequences encoding 2,3-dihydroxybenzoic acid decarboxylase may be expressed. The 2,3-dihydroxybenzoic acid decarboxylase is then isolated from the bacteria through protein purification techniques. Through this process, 2,3-dihydroxybenzoic acid decarboxylase can be produced in large quantities for use in industry and research. Additionally, it is known to those skilled in the art that there are several methods besides transformation with expression vectors that allow the expression of protein from a given nucleic acid sequence. One example is transfection of certain host cells with RNA. In another example, expression may be achieved from a nucleic acid sequence in vitro rather than in vivo. Host cells containing a nucleic acid sequence of interest can, in some instances, be used directly to carry out the reaction of interest. Thus, transformed cells may be used to directly catalyze the conversion of 2,3-dihydroxybenzoic acid decarboxylase to catechol.

The present invention discloses the product of the above-discussed method. This product is an isolated protein that decarboxylates 2,3-dihydroxybenzoic acid. This isolated product can be used in industry to catalyze the formation of catechol from 2,3-dihydroxybenzoic acid.

The present invention discloses a method for removing a ring mounted carboxyl group by non-oxidative decarboxylation. This is accomplished by causing a host cell to produce a protein having a biological activity substantially equal to 2,3-dihydroxybenzoic acid decarboxylase wherein said protein is encoded by a first nucleic acid sequence that hybridizes to a second nucleic acid sequence comprising SEQ ID NO: 1 under stringent conditions. This protein is then combined with molecules having a ring mounted carboxyl group and allowed to react under decarboxylation conditions to accomplish the non-oxidative decarboxylation.

The present invention discloses isolated nucleic acid sequences that encode 2,3-dihydroxybenzoic acid decarboxylase. The procedures listed below may be implemented to produce large quantities of the disclosed nucleic acid sequences. Additionally, these sequences can be produced through either synthetic or recombinant means. These procedures allow the industrial and scientific community access to the nucleic acid sequence of the present invention for further studies or for the purpose of expression in order to produce and isolate 2,3-dihydroxybenzoic acid decarboxylase.

Characterization of the Nucleic Acid Sequence Encoding 2,3-Dihydroxybenzoic Acid Decarboxylase The recombinant nucleic acid sequence, SEQ. ID. NO. 1, consists of an open reading frame of 1029 nucleotides. The start codon is at ATG and the stop codon at TAG. The conceptual translation product of this open reading frame is a protein, 342 amino acids in length. The length of 342 amino acids is as expected for a subunit size of 38,000 that has been determined by SDS-PAGE for the wild type enzyme protein from *Aspergillus niger*. The calculated molecular weight of the translated product is 39155.45 Da. This is similar to the molecular weight of 39,162 Da determined by mass spectrometric measurements for the wild type enzyme protein of *Aspergillus niger*. All partial sequences determined for this protein by amino acid sequencing, have been identified in this open reading frame. These partial sequences are illustrated in Santha et al., *Eur.J.Biochem*, 230, p. 104–110, 1995, which is hereby incorporated by reference. In particular, the N-terminal sequence is identical to that determined for the wild type protein from *Aspergillus niger*. Additionally, the sequence of the last four amino acids at the C-terminus of the protein was determined a through C-terminal sequencing of the native protein from *Aspergillus niger*. The identical amino acid sequence was discovered at the end of the reading frame in the recombinant nucleic acid sequence. The identity of three residues in the rest of the protein is different between the translated sequence and the protein sequence determination. These differences are, in some instances, due to errors in reading of sequencing results and, in some instances, due to the ambiguity in the determination of Asp and Cys on the protein sequencing machine used for the purpose. Another feature to note is that the translated product of the recombinant nucleic acid sequence contains the active site peptide with the Cys at the expected position as described in the above reference. This confirmed that the insert contained the coding sequence for 2,3-dihydroxybenzoic acid decarboxylase.

Characterization of Recombinant 2,3-Dihydroxybenzoic Acid Decarboxylase

Recombinant 2,3-dihydroxybenzoic acid decarboxylase is comparable to the wild type, or naturally occurring, *Aspergillus niger* 2,3-dihydroxybenzoic acid decarboxylase. For example, both enzymes catalyze the conversion of 2,3-dihydroxybenzoic acid to catechol. Neither the recombinant nor the wild type requires an externally added cofactor or metal ions for activity. The recombinant enzyme, like the wild type, is very stable.

Sequence comparisons were performed to determine the similarities in the sequences between the wild type and the recombinant. The recombinant protein was sequenced from the N-terminus and the first 20 amino acids were determined. This sequence was identical to that of the wild type protein.

The molecular weight of the wild type and the recombinant were compared on SDS gels. The recombinant protein and the wild type protein from *Aspergillus niger* comigrate on SDS gels at approximately 38,000 Da. Therefore, the subunit molecular weight of the recombinant enzyme is similar to the wild type at 38,000 Da.

The kinetic constants for both the wild type enzyme and the recombinant enzyme are similar. The recombinant enzyme has a $K_m$ of 0.35 mM which is comparable to a $K_m$ of 0.43 mM for the wild type enzyme from *Aspergillus niger*. The $^{13}C$ kinetic isotope effect, KIE, for the wild type enzyme was 1.031±0.001 at the optimum pH of 5.2, and under similar conditions, the KIE for the recombinant enzyme was 1.033, as reported in Santha et al., *FASEBJ*, 11, p A1017, abstract #932, 1997, poster presented at the 17$^{th}$ IUBMB Congress, San Francisco, which is hereby incorporated by reference.

The immunochemical cross reactivity was compared between the recombinant and the wild type from *Aspergillus niger*. Antibodies raised in rabbit to the wild type protein from *Aspergillus niger* successfully identify the recombinant protein during standard western blot procedures.

Additional Characteristics of Wild Type 2,3-Dihydroxybenzoic Acid Decarboxylase from *Aspergillus Niger*

2,3-dihydroxybenzoic acid decarboxylase operates in the fungal pathway for the degradation of indole in *Aspergillus niger*. Its existence has also been demonstrated in *Aspergillus oryzae* and *Trichosporon cutaneum*. The enzyme non-oxidatively decarboxylates 2,3-dihydroxybenzoic acid to form catechol and carbon dioxide. The enzyme does not require any externally added cofactor or metal ions for its activity. The enzyme was assayed spectrophotometrically by following the disappearance of 2,3-dihydroxybenzoic acid at 305 nm and by the appearance of catechol at 276 nm. The $K_m$ of the enzyme for 2,3-dihydroxybenzoic acid is 0.43 mM at a pH of 5.2. The enzyme appears to be specific for 2,3-dihydroxybenzoic acid and does not appear to decarboxylate salicylic acid(2-hydroxybenzoic), 2,4-dihydroxybenzoic acid or 3,4-dihydroxybenzoic acid.

The native molecular weight ($M_r$) for 2,3dihydroxybenzoic acid decarboxylase as assessed by gel filtration on a Sephacryl S-200 column is 150,000 Da. SDS gels of the protein illustrate a single band of 38,000 Da. Thus, the protein is a homotetramer of subunit size approximately 38,000 Da.

2,3-dihydroxybenzoic acid decarboxylase has an optimal activity at a pH of 5.2. Substantial activity (80–90%) is found in a range between pH 5 and 5.5. In addition, the enzyme is stable to at least a pH of 7.5.

The temperature for optimal activity of the enzyme increases with temperature to 50° C., after which the activity begins to decrease due to denaturation of the protein. Additionally, the enzyme is stable at temperatures above 50° C. in the presence of substrate analogs. One example of a substrate analog is salicylate. Assays were routinely done at 30° C. Enzyme purification was done at 4° C.

It has been found that certain modifying reagents, such as histidine, cysteine and tryptophan inactivate 2,3- dihydroxybenzoic acid decarboxylase. This inactivation may be due to the modification of one or more amino acids at or near the active site of the enzyme.

The following discussion will assist in defining the structure for a portion of the claimed invention. The genetic code is degenerate. This is because there are several combinations of three nucleotides that will code for the same amino acid. For example, Leu can be coded for by 6 combinations of 3 nucleotides. Many nucleic acid sequences can code for a particular amino acid sequence. Thus, there is a multitude of nucleic acid sequences that could code for SEQ. ID. NO. 2. It is intended that at least those nucleic acid sequences that both hybridize under stringent conditions with the nucleic acid sequence comprising SEQ. ID. NO. 1 and code for a peptide having substantially the same biological activity as 2,3-dihydroxybenzoic acid decarboxylase are included within the scope of this invention.

Stringent conditions are defined as hybridization in a medium containing 6×SSC or 6×SSPE and 40% formamide at a temperature of 37° C. and a wash at 37° C. with 2×SSC or 2×SSPE containing 0.1% SDS. These solutions were prepared from 20×SSC or SSPE which comprise the following compositions. The 20× SSC is formed by mixing 175.3 g of sodium chloride and 88.2 g of sodium citrate in 1 L of water with a final pH of 7.0. The 20× SSPE is formed by mixing 175.3 g of sodium chloride and 88.2 g of sodium citrate in 1 L of water with a final pH of 7.4. Any nucleic acid sequences that hybridize to SEQ.ID.NO.1 in a solution containing 6×SSC or 6×SSPE and 40% formamide at 37° C. and remains bound to SEQ.ID.NO. 1 when the milieu is changed to 2×SSC or 2×SSPE containing 0.1% SDS are those nucleic acid sequences defined as hybridizing under stringent conditions. Additionally, it is well known in the art that several factors affect hybridization including the length and nature of the probe, nature of the target, concentrations of salts, components in the hybridization solution, and temperature. Therefore, this description of stringency includes equivalent hybridization and wash conditions.

In describing the nucleic acid sequences of the present invention, both structure and function are utilized. The structure is provided by the above description of stringency; those nucleic acid sequences that hybridize under stringent conditions. The function is provided by the above discussion of the biological activity of 2,3-dihydroxybenzoic acid decarboxylase. Therefore, those nucleic acid sequences that hybridize to SEQ.ID.NO.: 1 and whose protein products have activity similar to 2,3-dihydroxybenzoic acid decarboxylase are included within the scope of the present invention. Additionally, those nucleic acid sequences that hybridize to SEQ.ID.NO.: 1 and whose protein products have activity similar to 2,3-dihydroxybenzoic acid decarboxylase may code for peptide fragments and are also included within the scope of the present invention.

Those of ordinary skill in the art will recognize that methods for vector construction and protein expression provided in the following examples are the preferred embodiment and that there are other techniques, vectors, and cell lines that could be implemented for constructing and expressing proteins or fragments thereof in either procaryotic or eukaryotic systems. The preferred embodiment disclosed herein does not limit the scope of the invention. There are a variety of alternative techniques and procedures available to those with ordinary skill in the art that would permit one to perform modifications on the present invention. It is also well known in the art that commercially available kits allow the modification and incorporation of the present invention. It is further recognized that those with ordinary skill in the art could employ any of a number of known techniques to modify the nucleic acid sequences of the present invention, in vitro or in vivo, and develop them further by established protocols for gene transfer and expression.

Several advantages are achieved by utilizing the present invention. For example, one advantage is that recombinant technology allows for the production of large quantities of 2,3-dihydroxybenzoic acid decarboxylase for commercial and scientific use.

Another advantage realized by the present invention is that it offers an enzyme that is capable of decarboxylating aromatic acids without the aid of any cofactor. This feature of non-requirement for a cofactor is an advantage when compared to traditional chemical procedures that require metals.

Another advantage realized by the present invention is that it offers enzyme based chemical procedures. Enzyme based chemical procedures are environment friendly and cost effective unlike typical chemical procedures that are associated with environmental concerns.

Another advantage realized by the present invention is that 2,3-dihydroxybenzoic acid decarboxylase may be utilized with other procedures for the production of catechol. This combination of procedures will create alternate methods for the synthesis of catechol that will not depend on fossil fuels.

EXAMPLE I

Growth of *Aspergillus Niger*

*Aspergillus niger* was grown on Byrde's modified synthetic medium containing anthranilic acid which served as an inducer of 2,3-dihydroxybenzoic acid decarboxylase as well as a nitrogen source for the growth of the organism, as illustrated by Kamath et al., *Applied and Environmental Microbiology*, January 1990, p. 275–280, which is hereby incorporated by reference. The medium composition per liter of water was as follows: glucose (5 g), anthranilic acid (2 g), potassium dihydrogen phosphate ($KH_2PO_4$, 5 g), magnesium sulfate ($MgSO_4.7H_2O$, 1 g), sodium sulfate ($Na_2SO_4$, anhydrous, 1 g) and trace element mixture (5 ml consisting of $FeCl_3.6H_2O$, 20 mg; $ZnSO4.10H_2O$, 10 mg; $MnSO_4.4H_2O$, 3 mg; $Na_2MoO_4.2H_2O$, 1.5 mg and $CuSO_4.5H_2O$, 0.1 mg). Trace elements were added from a 200× stock after the anthranilic acid had dissolved completely. The pH of the medium was adjusted to 5.5 with 3N NaOH. Sterile medium contained in Erlenmeyer flasks, 10% of the total flask volume, was inoculated with a dense spore suspension and the cultures left to grow under stationary conditions at 30° C. White mycelial felts were harvested at 24–26 hours after inoculation. The spent medium was decanted off. The mycelia were washed thoroughly in distilled water, dried between folds of Whatman paper 3MM and frozen in liquid nitrogen. Frozen mycelia were stored at −70° C. until further use for the isolation of RNA.

EXAMPLE II

Isolation of a Gene for 2,3-Dihydroxybenzoic Acid Decarboxylase

Isolation of mRNA

Total *Aspergillus niger* RNA was isolated from the frozen samples of Example I. These samples are ground in liquid nitrogen and the total RNA extracted utilizing the TRIzol™ reagent described in the LIFE TECHNOLOGIES™ protocol, revision date Dec. 22, 1993, which is hereby incorporated by reference. mRNA was isolated from the total RNA utilizing the procedures provided with FAST TRACK® 2.0 kit from INVITROGEN®. FAST TRACK® 2.0 kit manual version B, 160228 is hereby incorporated by reference.

Reverse Transcriptase-Polymerase Chain Reaction (RT-PCR) of mRNA

The mRNA was reverse transcribed to generate full-length first strand cDNA molecules using the procedures provided with the cDNA CYCLE® kit for RT-PCR from INVITROGEN®. The manual for the cDNA CYCLE kit version A, 150525 is hereby incorporated by reference. Features that relate to the experiment described here are the use of 1 µg of mRNA and the use of oligonucleotide represented in SEQ. ID. NO. 3 in place of the oligo dT provided with the kit. The oligonucleotide of SEQ. ID. NO. 3 is also an oligo dT primer, but has additional bases that represent a Not I restriction endonuclease site. This site was used in later cloning procedures.

The products of the reverse transcriptase reaction were utilized as templates in a PCR reaction designed to specifically amplify the nucleic acid sequence corresponding to 2,3-dihydroxybenzoic acid decarboxylase. This was accomplished by the use of a degenerate oligonucleotide primer constructed to represent the coding sequence of the N-terminus of 2,3-dihydroxybenzoic acid decarboxylase from *Aspergillus niger*. This oligonucleotide is represented by SEQ.ID.NO. 4. The sequence of the N-terminus is illustrated in Santha et al., *Eur.J.Biochem*, 230, p. 104–110, 1995, which is hereby incorporated by reference. For the construction of the primer, a codon usage table for the genus Aspergillus was created using the Genetics Computer Group (GCG) sequence analysis package. The codon frequencies for the amino acids at the first six positions of the N-terminus were evaluated to determine the best choice of degenerate oligonucleotides to represent the N-terminus. Degenerate first or third bases were used at positions with codon frequencies equal to or lesser than 0.5. The primer ended with the first two, instead of three bases for Ala, in order to provide a 3' GC 'clamp' for priming. In addition to this degenerate sequence, SEQ.ID.NO.4 comprised of bases at the 5' end that represent the EcoRI restriction endonuclease site. This site was used in cloning procedures.

The N-terminal specific oligonucleotide represented by SEQ.ID.NO.4 was used along with the oligo dT primer represented by SEQ.ID.NO.3 to amplify the products of the reverse transcriptase reaction using Taq polymerase. Conditions for the PCR reaction were as follows: 100 ng reverse transcribed product from 100 ng of starting mRNA, 10 µl PROMEGA® 10× PCR buffer mix (without $Mg^{2+}$), 15 pmol SEQ.ID.NO.3, 15 pmol SEQ.ID.NO.4, 0.5 U Taq polymerase from PROMEGA®, 2 mM $Mg^{2+}$, 0.2 mM dNTPs and $H_2O$ in a final reaction volume of 100 µl. The reaction mix without the $Mg^{2+}$ and the dNTPs was incubated at 80° C. for 1 min before starting the reaction by the addition of the $Mg^{2+}$-dNTP mix. The PCR cycling was performed in two stages. The first stage consisted of 5 cycles of denaturation at 94° C. for 1 minute, annealing at 45° C. for 1 minute and extension at 72 ° C. for 1 minute. The second stage consisted of 25 cycles of denaturation at 94° C. for 1 minute, annealing at 64° C. for 1 minute and extension at 72° C. for 1 minute. The cycling reaction was allowed to proceed to completion by a further incubation at 72° C. for 7 minutes. An agarose gel analysis revealed that a single product of size 1.1–1.2 kb was formed. This product was gel purified using the GENECLEAN® kit from Bio 101. The protocol for the GENECLEAN® Kit, Revision No. 1001-699-5F01, is hereby incorporated by reference.

Cloning of PCR Product

The PCR amplified nucleic acid sequences were then cloned into a pCR™II vector utilizing the procedures provided with a TA CLONING® Kit from INVITROGEN®. The TA CLONING® Kit, Version B, 150626, is hereby incorporated by reference. Ligation products or plasmid DNA used in this experiment, and at all stages throughout this study, were isolated according to established procedures. These procedures include transformation into a host such as *E. coli* DH5αF' cells, TOP10F' or INVαF' cells from INVITROGEN® or Novablue cells from NOVAGEN® and preparation of the plasmid using the NUCLEOBOND® kit from CLONTECH®. Procedures for transformation are outlined in the TA CLONING® Kit, Version B, 150626 from INVITROGEN and the pET System Manual, 6th Edition, TB055 8/95, provided by NOVAGEN®, respectively. Both these manuals and the NUCLEOBOND® nucleic acid purification tools user manual, PT3167-1 (PR84333), are hereby incorporated by reference. Plasmids were tested for insert size. Several positive clones were obtained and these were sequenced. Sequencing of these and several other clones described hereafter, was carried out at the DNA Sequencing Core Facility at the University of Nebraska-Lincoln Center for Biotechnology. Automated DNA sequencing was performed on LI-COR Model 4000 and LI-COR Model 4000L DNA sequencers using fluorescent primers in the dideoxy chain termination method. The sequences of the inserts, in all clones, contained the sequence described in SEQ ID NO. 1. In addition, there was an Eco RI restriction site before the start codon and a Not I site after the poly A stretch. These vectors were designated as pTA-DHBD-EcoRI.

EXAMPLE III

Expression of the Gene for 2,3-Dihydroxybenzoic Acid Decarboxylase

Preparation of the Insert for Cloning into pET22b(+)

A nucleic acid insert containing SEQ.ID.NO. 1 was generated from pTA-DHBD-EcoRI. This insert contained a Nde I restriction site located at the initial ATG instead of the EcoRI restriction site found in pTA-DHBD-EcoRI. The insert was generated through PCR with pTA-DHBD-EcoRI as a template, and oligonucleotides represented in SEQ.ID.NO. 3 and SEQ.ID.NO.5 as primers. Reaction conditions were the same as described above for RT-PCR of mRNA. A single product of size 1.1–1.2 kb was obtained. The insert was purified from a gel using the GENECLEAN® kit from Bio 101 as discussed above. The purified product was cloned into a TA vector, pCR™II vector of INVITROGEN® using the TA CLONING® kit from INVITROGEN® as discussed above. Several positive clones with inserts of the proper size and sequence were obtained. The insert sequence for this vector contains a sequence identical to SEQ.ID.NO.:1. Additionally, the insert had an Nde I site overlapping the initial ATG and a Not I site after the poly A tail. This vector was designated pTA-DHBD-NdeI.

Cloning into the Expression Vector pET22b(+)

The insert from pTA-DHBD-Nde I, which contained a sequence identical to SEQ.ID.NO.1, was released from the vector by enzymatic digestion with restriction endonucleases Nde I and Not I. The insert was gel purified by the GENECLEAN® method referenced above. Purified inserts were ligated and cloned in a pET22b(+) vector that was subjected to enzymatic digestion with the same restriction endonucleases, Nde I and Not I. The resulting vector contained the insert for 2,3-dihydroxybenzoic acid decarboxylase positioned at the Nde I site. This positioning ensured that the start codon ATG was positioned at an appropriate distance from the T7 promoter and that the coding sequence was in the correct reading frame for the protein to be expressed. This vector was designated pET-22b(+)DHBD.

Expression of Recombinant 2,3-Dihydroxybenzoic Acid Decarboxylase

Expression of 2,3-dihydroxybenzoic acid decarboxylase was achieved by transforming pET22b(+)DHBD into an E.coli expression host, BL21(DE3). The procedures for transformation and expression were performed according to the pET System Manual, 6th Edition, provided by NOVAGEN®, TB055 8/95, which is also covered by U.S. Pat. No. 4,952,496. Both the manual and the patent are hereby incorporated by reference. Transformed cells were grown at 37° C. in Luria Broth medium containing ampicillin and chloramphenicol to an absorbance at 600 nm of 0.6–1.0. Cells were induced with isopropyl-β-D-thiogalactoside (IPTG) at a concentration of 0.4 mM and allowed to incubate with shaking at 37° C. for another 3 hours at which point the cells were harvested. The harvested cells were stored at −20° C. These cells were used for the isolation of 2,3-dihydroxybenzoic acid decarboxylase.

EXAMPLE IV

Isolation of Recombinant 2,3-Dihydroxybenzoic Acid Decarboxylase

Cells induced for expression of 2,3-dihydroxybenzoic acid decarboxylase, as described above in Example III, were suspended in an equal volume of 50 mM sodium phosphate buffer, pH 7.0, containing protease inhibitors. These protease inhibitors included pepstatin (10 μg/ml), leupeptin (10 μg/ml), phenylmethanesulfonyl fluoride (1 mM), 1,10-phenanthroline (5 mM) and EDTA (1 mM). The suspension was sonicated in 3 pulsed cycles at 2 minute intervals. The 2,3-dihydroxybenzoic acid decarboxylase was purified from this lysate using a combination of ion exchange chromatography and affinity chromatography. Purified preparations were determined to be homogenous by SDS-PAGE and N-terminal sequencing. The above procedure is described by Santha et. al., *Biochimica et Biophysica Acta*, 1293, 1996, p. 191–200, and references therein. This publication is hereby incorporated by reference.

EXAMPLE V

Preparation of Multiple Copies of Vectors Containing Inserts

Multiple copies of vector containing insert, for example, pET22b(+)DHBD, were prepared by transformation of Novablue® cells as described in the pET System Manual, 6th Edition, TB055 8/95, provided by NOVAGEN®, which is hereby incorporated by reference. Multiple copies of pTA-DHBD-EcoRI or pTA-DHBD-Nde I, were prepared by transformation of TOP10F' or INVαF' cells as described in the TA CLONING® kit manual, Version B, 150626 from INVITROGEN, which is hereby incorporated by reference.

All references discussed herein are specifically incorporated in their entirety in all respects.

From the foregoing, it may be seen that this invention is one well-adapted to achieve all the ends and objects hereinabove set forth together with other advantages which are obvious and which are inherent to the invention. It will be understood that certain features and subcombinations are of utility and may be employed without reference to other features and subcombinations. The above examples discuss the techniques and procedures utilized and are considered to be the preferred embodiment of the current invention, and it is understood that there are many other techniques and procedures that could be employed which would allow an individual of ordinary skill in the art to perform the claimed invention Such other techniques and procedures are contemplated by and are within the scope of the claims. Since many possible embodiments may be made of the invention without departing form the scope thereof, it is to be understood that all matter herein set forth and shown in the drawings and examples are to be interpreted as illustrative and not in a limiting sense.

I claim:

1. An isolated nucleic acid sequence comprising SEQ ID NO: 1.

2. An isolated nucleic acid sequence encoding a protein comprising SEQ ID NO: 2.

3. A vector comprising an isolated nucleic acid sequence encoding a protein comprising SEQ ID NO: 2.

4. The vector of claim 3 wherein the vector contains regulatory elements operably linked to the isolated nucleic acid.

5. A host cell comprising an isolated nucleic acid sequence encoding a protein comprising SEQ ID NO: 2.

6. A method of producing an isolated polynucleotide which encodes a protein comprising SEQ ID NO: 2 comprising:

a) culturing the host cell of claim 5 to produce the polynucleotide; and b) isolating the polynucleotide.

* * * * *